United States Patent
Petruzzello et al.

(10) Patent No.: US 8,137,276 B2
(45) Date of Patent: Mar. 20, 2012

(54) METHOD AND APPARATUS FOR GUIDANCE AND APPLICATION OF HIGH INTENSITY FOCUSED ULTRASOUND FOR CONTROL OF BLEEDING DUE TO SEVERED LIMBS

(75) Inventors: John Petruzzello, Carmel, NY (US); Helen Routh, New York, NY (US); John Fraser, Woodinville, WA (US); Shervin Ayati, Carlisle, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 954 days.

(21) Appl. No.: 12/096,752

(22) PCT Filed: Dec. 7, 2006

(86) PCT No.: PCT/IB2006/054669
§ 371 (c)(1),
(2), (4) Date: Jun. 9, 2008

(87) PCT Pub. No.: WO2007/069154
PCT Pub. Date: Jun. 21, 2007

(65) Prior Publication Data
US 2008/0306414 A1    Dec. 11, 2008

(51) Int. Cl.
*A61B 8/00* (2006.01)

(52) U.S. Cl. ........ 600/439; 600/407; 600/437; 600/453; 600/454

(58) Field of Classification Search .......... 600/407, 600/437, 439, 453, 454
See application file for complete search history.

(56) References Cited

U.S. PATENT DOCUMENTS

| | | | |
|---|---|---|---|
| 4,667,679 A * | 5/1987 | Sahota | 600/407 |
| 5,555,886 A * | 9/1996 | Weng et al. | 600/454 |
| 6,432,067 B1 | 8/2002 | Martin et al. | |
| 2003/0139766 A1 | 7/2003 | McEwen et al. | |
| 2007/0004984 A1 * | 1/2007 | Crum et al. | 600/471 |
| 2007/0066897 A1 * | 3/2007 | Sekins et al. | 600/437 |

FOREIGN PATENT DOCUMENTS

| | | |
|---|---|---|
| DE | 10209380 A1 | 9/2003 |
| EP | 0679371 A1 | 11/1995 |
| GB | 1259631 A | 1/1972 |
| WO | 01/34018 A | 5/2001 |
| WO | 2005/037060 A | 4/2005 |

* cited by examiner

OTHER PUBLICATIONS

Martin, R.W., et al., "Hemostatis of Punctured Vessels Using Doppler-Guided High-Intensity Ultrasound," Ultrasound in Medicine and Biology, New York, NY, US, vol. 25, No. 6, Jul. 1999, pp. 985-990, XP004295429.

*Primary Examiner* — Brian Casler
*Assistant Examiner* — Jason Ip
(74) *Attorney, Agent, or Firm* — W. Brinton Yorks, Jr.

(57) ABSTRACT

An ultrasonic diagnostic and therapy system is described for stopping the bleeding of severely damaged bloodvessels or vessels severed in a limb amputation. A cuff (30) is attached to the stump of the severed limb which contains a diagnostic transducer array and a HIFU transducer (42, 44). The diagnostic transducer surveys the tissue of the severed limb, searching for a Doppler flow signal. When a Doppler flow signal is detected, the range to and coordinates of the sample volume where the flow was detected are determined, as well as the flow velocity. This information is supplied to a HIFU therapy transducer controller, which controls the HIFU transducer to transmit focused ultrasound to the sample volume of the flow locus, the center of the lumen of a blood vessel. The focused ultrasound heats and coagulates blood in the severed vessel to stem the bleeding.

16 Claims, 9 Drawing Sheets

METHOD AND APPARATUS FOR GUIDANCE AND APPLICATION OF HIGH INTENSITY FOCUSED ULTRASOUND FOR CONTROL OF BLEEDING DUE TO SEVERED LIMBS

This invention relates to medical diagnostic and therapeutic ultrasound systems and, in particular, to methods and apparatus for controlling bleeding from severed blood vessels with high intensity focused ultrasound.

Battlefield trauma injuries involving proximal amputation of limbs are common in warfare. Severed limbs can also occur in automobile and industrial accidents and from other causes. The major cause of loss of life in these cases is rapid exsanguination from the major arteries of the arm or leg, the brachial and femoral arteries, respectively. These wounds are very difficult to deal with in an emergency setting, as the crudely severed ends of the arteries do not spasm closed, and retract into the limb, making access to clamp them difficult or impossible. A method and apparatus for use at the scene of the injury by minimally trained emergency medical technicians is desired.

Application of high intensity focused ultrasound (HIFU) in the low MHz frequency range has been shown to reduce and eliminate bleeding in punctured and slashed arteries through the effects of heating the artery walls and the blood itself, albeit in smaller arteries and with slower flow than the larger arterial vessels mentioned above. Accordingly it is desirable to have apparatus and methods which can be used to treat bleeding from any peripheral vessel quickly and effectively in an emergency situation.

In accordance with the principles of the present invention therapy apparatus is described which uses a complete or partial cuff applied to the stump of an affected limb, including a flow sensing transducer and a high intensity ultrasound transducer. The two transducers are in a known relationship to each other so that the data of blood flow located or tracked by the flow sensing transducer can be used to guide the application of high intensity ultrasound to the blood flow. Supporting electronics for the transducers as well as a simple display mechanism can be located on the cuff or in an instrument attached to the cuff. The display allows rapid alignment by the operator of the cuff in proximity to the detected flow region (the target vessel). A flow processor connected to the flow sensing transducer provides automatic determination of the distance between the cuff and the target vessel. The high intensity ultrasound transducer may be an annular or linear array, and transmits one or more high intensity focused ultrasound (HIFU) spots, or a HIFU line beam, focused along the blood vessel at the depth determined by the flow processor to be appropriate.

In an example described below, multiple Doppler and HIFU phased arrays are used to automatically acquire locational and functional data of the high flow vessel for internal use by the system, and to transmit a tailored HIFU beam to heat the vessel along a segment of its length. Delivering HIFU energy along a length of a blood vessel can be significant to successful coagulation of blood in the severed vessel.

Acoustic coupling of the cuff transducers to the limb can be provided by an impedance matched pad or fluid-filled enclosure. The cuff can be used with coupling gel on the skin for rapid achievement of good ultrasound coupling over the extended area required.

Figure 1:
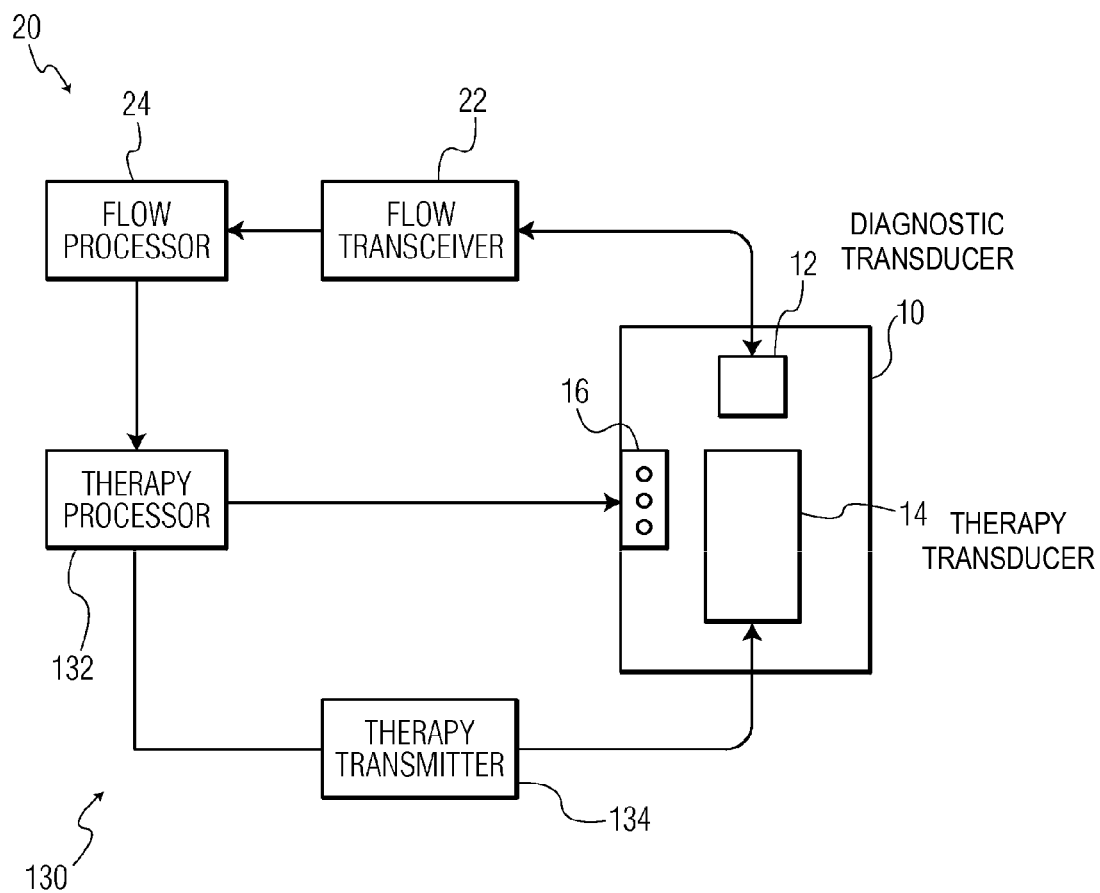
FIG. 1 illustrates in block diagram form an ultrasonic diagnostic and therapeutic system constructed in accordance with the principles of the present invention for treatment of severed blood vessels.

Referring first to FIG. 1, an ultrasonic diagnostic and therapeutic system constructed in accordance with the principles of the present invention for treatment of severed blood vessels is shown in block diagram form. A transducer cuff 10 which contacts the severed limb in the vicinity of a bleeding blood vessel contains a diagnostic transducer 12 and a therapy transducer 14. The diagnostic transducer locates the blood vessel, preferably by Doppler detection of the flow of blood. The diagnostic transducer is coupled to the diagnostic section 20 of the system. The diagnostic transducer is controlled by a flow transceiver 22 of the diagnostic section which actuates the transducer and receives echo signals from the blood vessel. The echo signal information is coupled to a flow processor 24 of the diagnostic section which determines the location of the blood vessel and, in examples described below, also the rate (velocity) of the blood flow. This blood flow information is coupled to a therapy processor 132 in the therapeutic section 130 of the system. The therapy processor 132 utilizes the information to control the delivery of ultrasonic therapy to the blood flow through control of a therapy transmitter 134 of the therapeutic section. High intensity ultrasound is focused on the blood of the blood vessel through use of the locational and flow information provided by the diagnostic transducer. Treatment proceeds until the blood in the vessel has been sufficiently coagulated to stem the flow of blood. A display indicator 16 which is shown located on the transducer cuff 10, but may alternatively be located on an instrument containing the diagnostic or therapeutic sections, provides visual guidance to the user in the placement of the transducer cuff in proximity to a flowing blood vessel and can also indicate when treatment is proceeding and has concluded. Alternatively or in addition to a visual indicator, audible instructions may be produced by the system to guide the user.

In use, the transducer cuff 10 is placed on or wrapped around the end of the severed limb. When a wrap-around cuff is used the cuff is inflated or tightened to be in good acoustic and stationary position on the skin of the patient and above a severed blood vessel. The diagnostic transducer locates the blood vessel, preferably by Doppler sensing of the highest flow velocity below the transducers. The location of the blood vessel is computed, as is the Doppler velocity of blood flow. This information is supplied to the therapy processor which controls the therapy transmitter to transmit high intensity ultrasound focused at the depth and lateral location of the blood vessel. The diagnostic transducer monitors the vessel during treatment. This monitoring can include continually tracking the location of the blood vessel to keep the therapy transducer focused on the appropriate area of the vessel, and monitoring the flow to determine when coagulation has occurred and the flow of blood has stopped and the treatment is finished. The diagnostic information can also be, but does not have to be, displayed if desired. In one example described below a length of the blood vessel is heated during treatment by delivering a line of heat align the blood vessel to coagulate the blood. In another example a spot of high intensity ultrasound is focused on a bolus of blood and moved with the blood flow to continuously heat the same bolus of blood as it moves through the blood vessel below the therapy transducer. These techniques are useful for overcoming the continual dissipation of heat in the vessel due to the high rate of blood flow carrying the heat through and out of the severed vessel. The application of the HIFU energy over an extended region of the artery allows the blood to be heated to a sufficient temperature to promote coagulation without exceeding the allowable thermal dose in the intervening tissue.

Numerous examples of a system of the present invention are illustrated and described below. In one example a partial cuff with a cylindrical array is used as the HIFU source so the X-Y location of a line focused ultrasound beam is set by the user moving the cuff on the skin surface. The user is guided by a simple user interface (e.g., a speedometer indicator or an array of colored LEDs) which give an indication of the skin location where the highest flow is detected. Duplicate diagnostic detector arrays at both ends and/or alongside the HIFU array enable alignment of the cuff in close proximity to the vessel being treated. The focal depth of the HIFU beam is set automatically by the transmitter circuitry driving the cylindrical therapy array, based on the range of the detected maximum Doppler signals at the multiple detector systems. This example uses a single large cylindrical array to deliver sufficient energy to provide coagulation over an extended region along the vessel.

In another example a transducer cuff of multiple phased arrays is applied to the limb so the whole volume is interrogated by means of electronic beam steering. The cuff is guided and positioned so that one or more therapeutic HIFU arrays are located parallel to the blood vessel. The therapeutic beam location for coagulation is determined by the high flow rate indicative of a severed vessel which is higher than the flow rate should be when the blood flow rate is moderated by the resistance of a capillary bed. There are also Doppler signal anomalies in the vicinity of the leak, and in the blood pool around where the leak has been flowing. In this case, delivering sufficient power to allow coagulation is achieved by the use of multiple transducers for therapeutic power generation.

Figure 2:
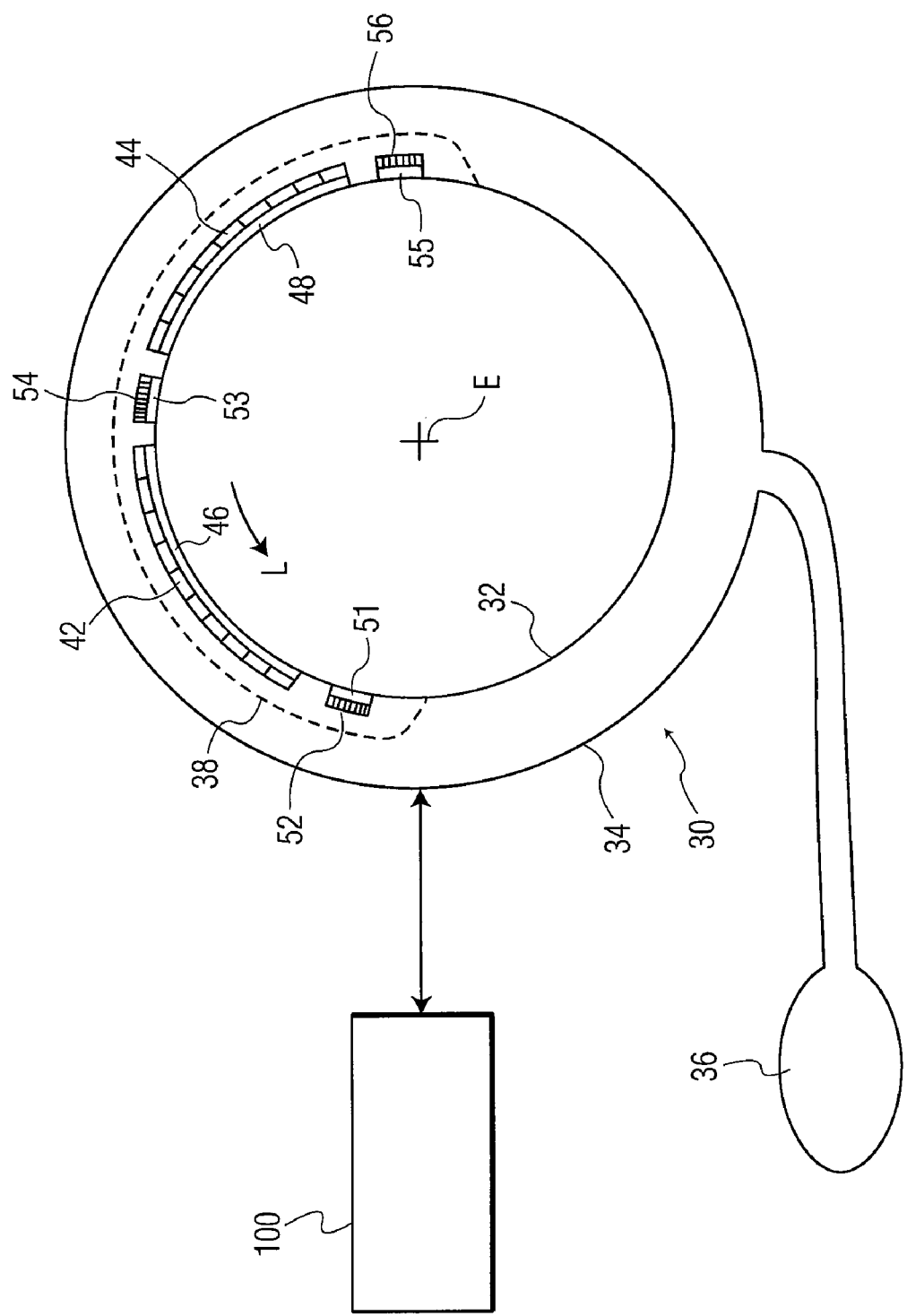
FIG. 2 illustrates one example of a transducer cuff constructed in accordance with the principles of the present invention.

FIG. 2 is one example of a transducer cuff 30 of the present invention. The cuff 30, shown here in cross-section, is an inflatable bladder-like sleeve similar to that used for blood pressure measurements. The cuff can be made in different sizes (diameters) for arm or leg use. In a cuff suitable for arm use the transducers may extend completely around the cuff or only a portion of the arc of the cuff such as an arc of transducers subtending 90° to 135° of arc. The illustrated example of FIG. 2 uses transducers subtending an arc of 135°. A suitable arc for the leg is approximately 9 cm by 9 cm. For the arm a suitable arc is approximately 6 cm by 6 cm. The cuff 30 has an inner surface 32 which contacts the limb of the patient and an outer surface 34. The space between these surfaces can be inflated with an inflation pump 36. Inflation of the cuff accomplishes three objectives: it presses the transducers on the inside of the cuff into good acoustic contact with the limb of the patient; it secures the transducers in a stationary position with respect to the underlying blood vessels; and it provides a tourniquet force around the limb to help stem the flow of blood. The tourniquet function can slow the flow of blood so that more time is available to diagnose and treat a bolus of blood within range of the transducers. A lower flow rate can also be treated effectively with a lower dose of acoustic energy. The cuff 30 is coupled to a therapy and diagnostic delivery system 100 which controls the diagnostic and therapy transducers. The transducers are attached to the inner surface of the cuff. Two cylindrically curved array therapy HIFU transducers 42 and 44 are located at the inner surface. Interspaced at the ends and between the HIFU transducers in this example are three two-dimensional phased array transducers 52, 54, and 56. All of the transducers are mounted so as to be well acoustically coupled to the limb of the patient inside the cuff. One way to provide acoustic coupling is to locate the transducers in a fluid-filled compartment. In this example a dotted line 38 represents a urethane membrane which encloses the transducers in a fluid-filled compartment between the membrane 38 and the inner surface 32 of the cuff 30. Another way to provide acoustic coupling is with an acoustic coupling pad located between the emitting surfaces of the transducers and the skin of the patient. In this example acoustic coupling pads 46, 48, 51, 53, and 55 are shown on the emitting surfaces of the transducers 42, 44, 52, 54, and 56. Separate pads or one continuous pad may be used. The acoustic coupling pads may be made of a solid cis-polybutadiene standoff material or a gel material such as Kitecko standoff pads.

The two dimensional phased array transducers 52, 54 and 56 are made of diced piezoelectric material. The HIFU transducer elements may be formed of solid piezoelectric material or a composite of piezoelectric ceramic and epoxy, which enables the curved HIFU arrays to be bent into the desired arcuate shape. The two dimensions of the array allow Doppler interrogation of a volume below the arrays so that the arrays can systematically search for a locus of high flow rate inside the limb. The HIFU transducers 42 and 44 are diced in their longitudinal dimension (indicated by the arrow L) so that the therapeutic beams can be focused at selected depths of focus below the skin surface where the blood vessels are located. The HIFU transducers 42, 44 can also be diced in the elevational direction (into the plane of the drawing as indicated at E) to enable steering and focusing of the therapeutic beams at selected beam angles where the vessels are located, and to track the flow of a bolus of blood through a vessel. The HIFU transducers are preferably quasi-air-backed to reduce significant heating in the backing. A thermally conductive matching layer and a support frame coated with a low impedance intermediate layer may be used for good heat transfer to the standoff pad and mechanical support for the HIFU transducers. The transducers are preferably backed with attached flip-chip microbeamformers to control operation of the transducers and to prevent significant energy loss between the driving circuitry and the transducer elements by driving the transducer elements directly. Suitable microbeamformers and microbeamforming techniques in general are described in U.S. Pat. No. 6,375,617 (Fraser), U.S. Pat. No. 5,997,479 (Savord) and U.S. Pat. No. 6,126,602 (Savord).

The therapy transducers 42, 44 are operated in a lower MHz range of 2.5 to 4 MHz, for instance. Even lower frequencies of 1.0 to 1.5 MHz may be preferred for very deep arterial vessels. The diagnostic transducers 52, 54, 56 are operated in this range or higher depending upon the desired range of operating depths, with lower frequencies being preferred for deeper leg depths and higher frequencies for shallower arm depths. The diagnostic transducers will generally be operated with a full aperture, with the therapy transducers operable with a full aperture or subapertures of groups of elements of the arrays. The drive pulses for the HIFU transducers may be pulse width modulated for improved efficiency.

Figure 3:
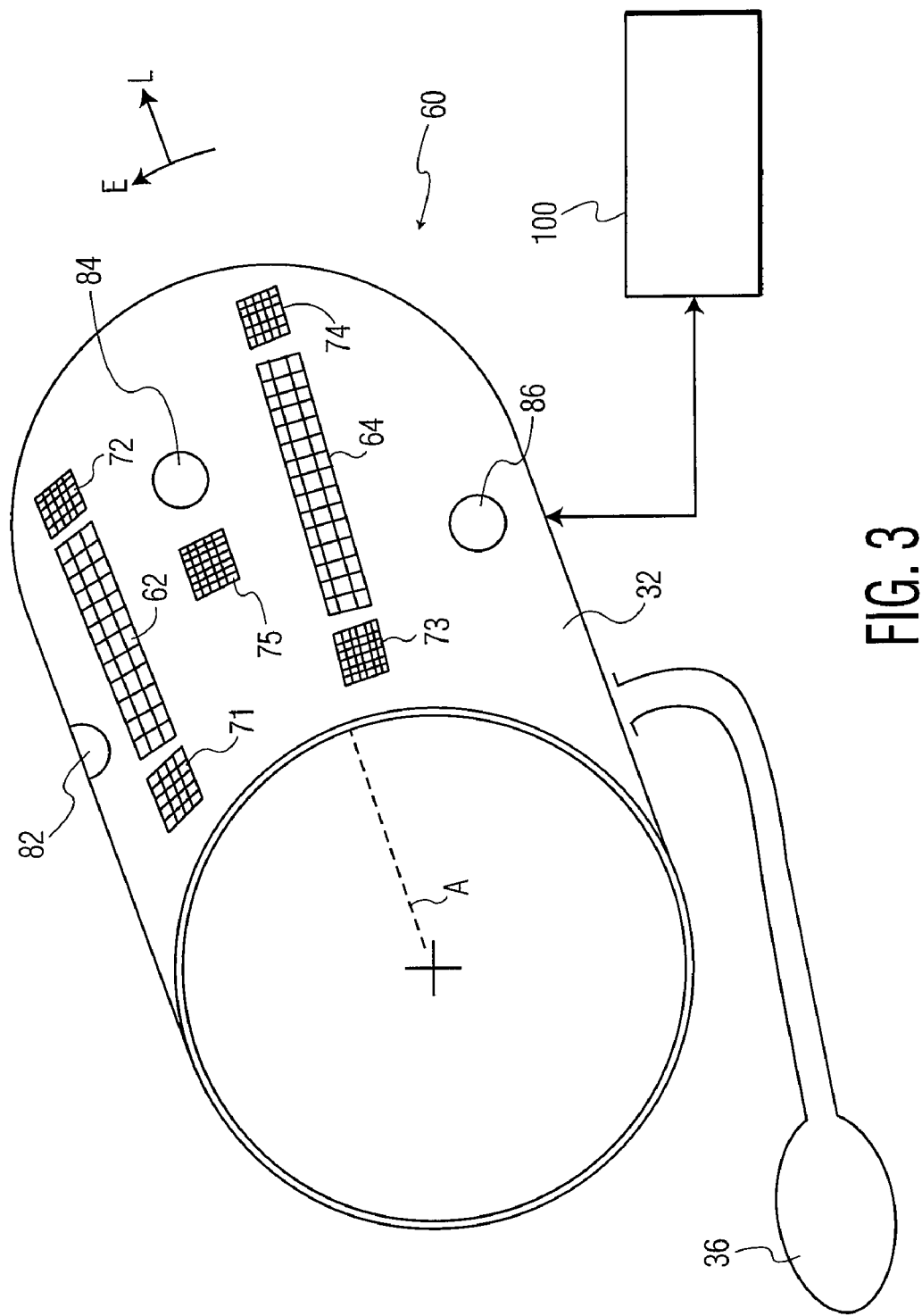
FIG. 3 illustrates a second example of a transducer cuff constructed in accordance with the principles of the present invention.

FIG. 3 illustrates in a perspective view a second example of a transducer cuff 60 of the present invention. In this example the outer surface 34 of the cuff has been removed to visualize the transducer arrays on the inner surface 32 of the cuff. The HIFU arrays 62 and 64 in this example are aligned with their longitudinal axes (as indicated by arrow L) parallel to the center axis A of the cuff. This orientation of the therapy arrays will tend to align them with blood vessels extending to the severed end of a limb, particularly the larger femoral and brachial arteries of the leg and arm. The 2D Doppler arrays 71, 72, 73, 74, and 75 are located at the ends of the therapy arrays, between the therapy arrays, or both as illustrated in the example of FIG. 3. The therapy arrays 62 and 64 are diced in both the longitudinal dimension L and in the elevational dimension E (indicated by arrow E) for full range of therapeutic beam focusing and steering. The transducer arrays are fabricated and acoustically coupled as described previously. Optionally, the cuff 60 may include one or more force or pressure sensors 82, 84 and 86 which are attached to the inner surface 32 of the cuff. These sensors may be piezoelectric elements or strain gauges which sense the force or pressure of the inner surface of the cuff against the limb. When the signals produced by these sensors fall below a predetermined limit, they produce an indication that the cuff has not been attached securely enough to the limb or is loosening, which will cause disruption of the acoustic coupling between the transducer arrays and the patient. The condition may be resolved by re-inflating the cuff 60.

Figure 4:
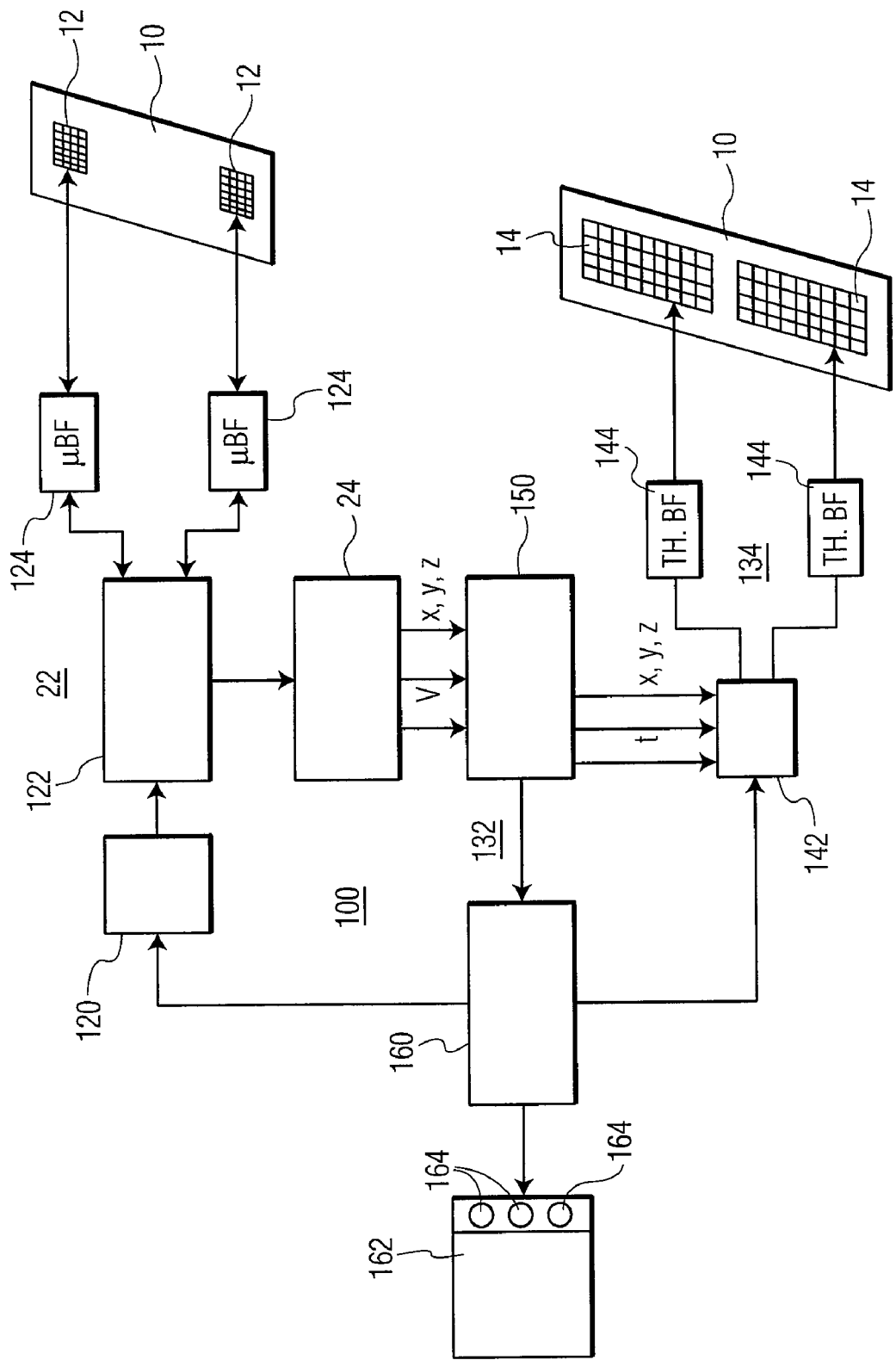
FIG. 4 is a detailed block diagram of the signal processing and control system of an ultrasonic diagnostic and therapeutic apparatus constructed in accordance with the principles of the present invention.

FIG. 4 is another example in accordance with the principles of the present invention in which the diagnostic and therapeutic sections of a therapy diagnosis and delivery system are shown in greater detail. A therapy controller 160 controls both aspects of the apparatus. The therapy controller 160 is coupled to an image drive 120 to command the image drive to produce drive signals for the diagnostic transducer arrays 12 of the cuff 10. The term "image" is not meant here to suggest that an ultrasound image is formed, as imaging is not necessary in an implementation of the present invention, Rather, the term here implies that the ultrasonic energy transmitted by the diagnostic arrays is in the power range used for diagnostic imaging and below the therapeutic energy range. The drive signals are provided to a transmit/receive controller 122 which in turn controls microbeamformers 124 to cause the diagnostic arrays 12 to methodically scan the volume below them, looking for a high intensity or velocity Doppler return. The echo signals received by the transmit/receive controller 122 are coupled to a Doppler processor which Doppler processes the echo signals from the transmitted and received beams as by FFT processing. When a severed blood vessel is within the range of one of the diagnostic arrays a strong or high velocity Doppler signal will be received from a sample volume located at a particular point in the limb inside a blood vessel. This indication may be communicated to the therapy controller 160 by the Doppler processor 24 as a "flow detected" signal, in which event the therapy controller will cause the "Flow" LED 164 on a display 162 to light. From the angle of the Doppler beam direction and the range (depth) from which the Doppler signal is returned, the x,y,z coordinates of the center of the blood vessel may be determined. The number of adjacent sample volumes from which the strong or high velocity Doppler signal is returned, or a computation of the volume flow, indicates the size of the blood vessel. This information, size, velocity (V), and location (x,y,z) are coupled to a therapy planner 150. Other echo signals may provide other information about the tissue between the blood vessel and the array such as the presence of foreign material such as shrapnel or glass, as well as tissue beyond the vessel which may be sensitive to treatment such as bone or nerves. The therapy planner uses this information to develop control signals for the therapy and signals the therapy controller 160 that a flow source has been located and that therapy can begin.

The therapy controller responds to this information by lighting the "Therapy" LED 164 on the display 162. The therapy controller commands a therapy drive 142 to commence operation and therapy begins. The therapy drive 142 provides drive signals to therapy beamformers 144. The drive signals cause therapeutic beams to be transmitted by a therapy array 14 at a power level determined by the information provided by the therapy planner 150. The power level will generally be a function of the size of the blood vessel (larger vessels requiring more power) and the flow rate (higher flow rates requiring more power). The therapy planner 150 provides the x,y,z location of the blood vessel center (where flow is greatest) which is used by the therapy drive 142 and therapy beamformers 144 to steer the therapy beams in the correct direction and focus the beams at the center of the blood vessel. A time signal t provides a time variation providing the length of time that the therapeutic beams are to be focused at the indicated location in the blood vessel.

Periodically the therapy controller 160 interrupts the therapy to command the diagnostic transducer array to resample the therapy area to make sure that the center of the blood vessel has not moved from its previously determined location. The velocity and direction of the blood flow indicate the location where a bolus of blood, found at an earlier point in time, is expected to be at a later point in time. The area around the is expected location is scanned by the diagnostic transducer and the nearest sample volume of greatest velocity and/or Doppler signal intensity is identified as the location where the previously heated bolus of blood may be found at the later (now current) point in time. The therapy planner 150 responds by appropriately adjusting the control parameters for the therapy drive 142 and beamformers 144. In this manner a bolus of blood may be initially heated as it comes within range of the arrays, and may be tracked and continue to be heated as it flows to the severed end of the blood vessel. This bolus of blood will be at a higher temperature, and thus more likely to precipitate coagulation, than would be a bolus of blood passing through a fixed focal point of the therapy array. In this manner the dissipation of heat by the flow of blood is addressed. Others who have studied the physiological phenomena involved in this process suggest that heating causes the vessel to shrink, slowing the flow, and the pool of blood around the severed end is coagulated to form a seal.

Figure 5:
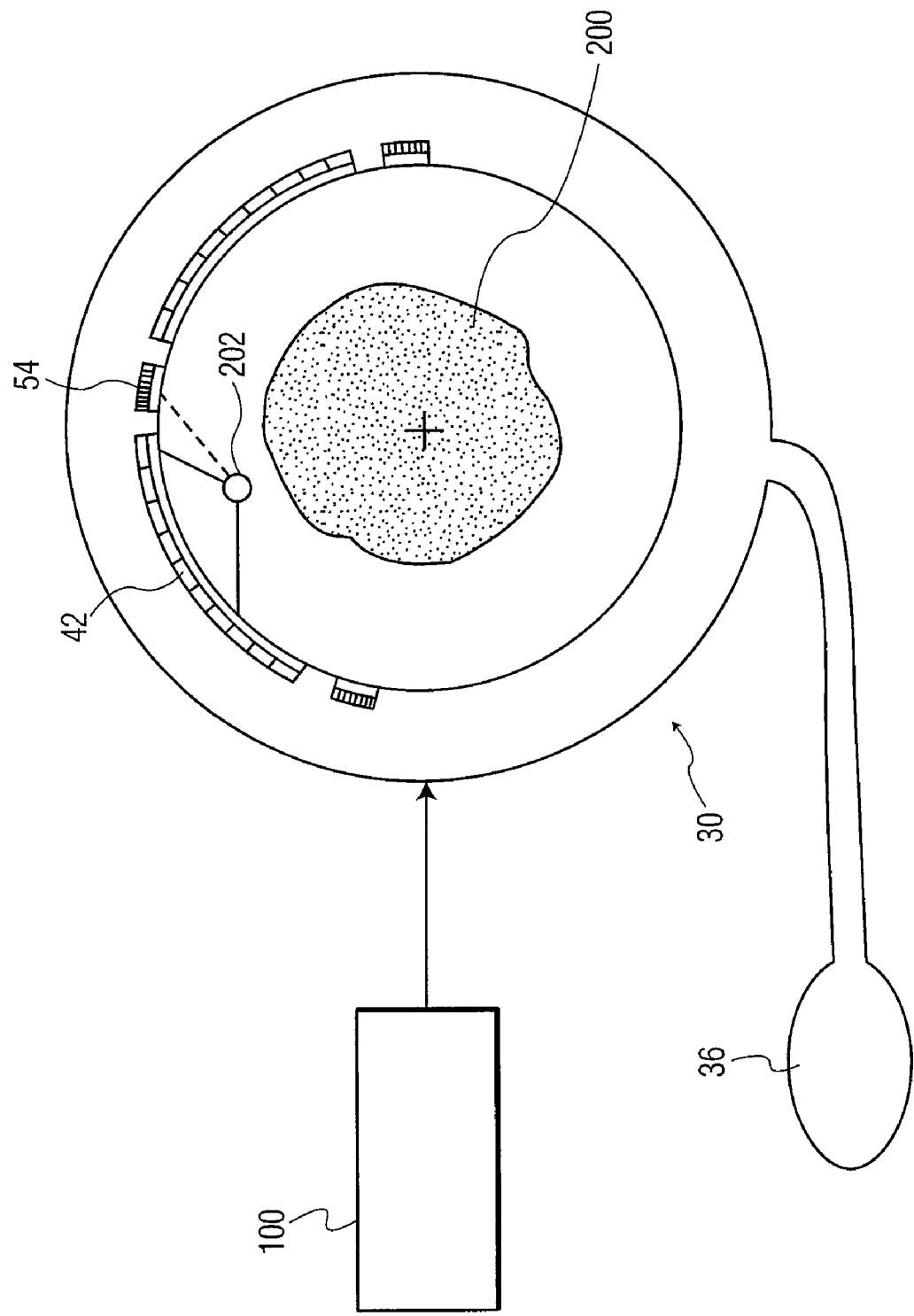
FIG. 5 illustrates one method of using the transducer cuff of FIG. 2 to heat the blood of a located blood vessel.

FIG. 5 illustrates how this procedure may occur through use of the transducer cuff of FIG. 2. Inside the inflated cuff 30 is a severed limb of the patient with a bone such as the femur 200 shown at the center of the limb. A blood vessel such as the femoral artery 202 is located in the volume of tissue surrounding the femur 200. The diagnostic transducer 54 has located the blood flow in the femoral artery 202 in the beam direction of the dashed line extending from the transducer array 54 to the femoral artery. The range (depth) and directional information of this beam is used to direct the aperture or a subaperture of the therapy array 42 to focus high intensity ultrasonic energy at the femoral artery as indicated by the solid lines extending form the therapy array 42 to the femoral artery 202. Since the therapeutic energy originates from an extended length of the array at the skin surface, the energy density is not sufficient to cause damage to the tissue between the therapy array 42 and the femoral artery 202. It is only when this energy comes into focus inside the blood vessel that the energy density become high enough to cause heating and the intended coagulation of blood in the severed vessel 202.

Figure 6:
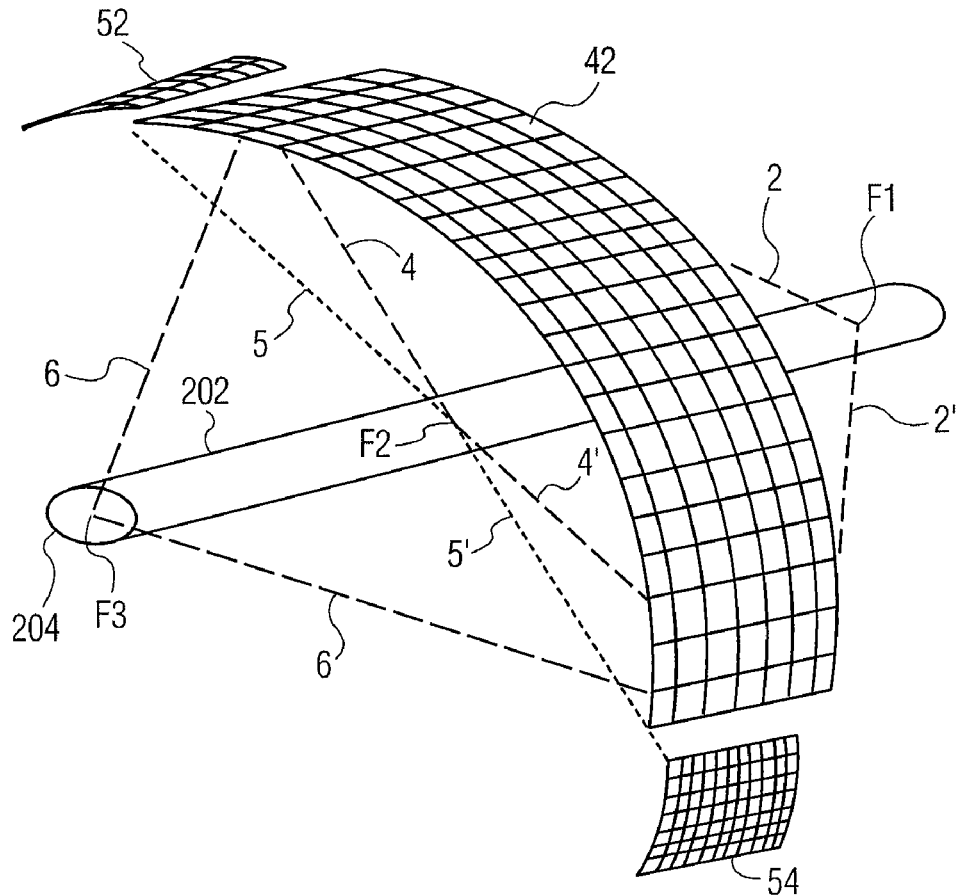
FIG. 6 illustrates a second method of using the transducer cuff of FIG. 2 to heat the blood of a located blood vessel.

FIG. 6 illustrates how the transducer arrays of the transducer cuff 30 track and heat a bolus of blood as it moves through a section of the artery 202 to its severed distal end 204. The blood flow of the vessel 202 is initially detected as it comes into range at a focal point F1. The segmentation of the curved 2D array 42 enables the therapeutic beam to be steered to and focused initially at the focal point F1 as indicated by dashed lines 2,2'. The velocity information indicates the speed at which the bolus of blood is moving through the blood vessel 202 and it is tracked and heated as it moves through the vessel. As a later time the bolus is at focal point F2, which is identified by the diagnostic arrays 52,54 as indicated by the dashed lines 5,5' extending from the diagnostic arrays. The diagnostically determined range and location information of the focal point F2 is used to cause the therapy array 42 to be focused at focal point F2 at this time as indicated by dashed lines 4,4'. Eventually the same bolus of blood is at the extreme of the transducer range, blood vessel, or both as indicated by focal point F3. The therapeutic beams are steered and focused at point F3 at this time as indicated by dashed lines 6,6'. Thus, the same bolus of blood is tracked and repeatedly or continuously heated as it progresses along a length segment of blood vessel 202. In this example it is seen that the diagnostic arrays are oriented toward each other so that their beams intersect in the region of the blood vessel 202. In this orientation the diagnostic arrays 52,54 may be operated in the pulse-echo mode in which each array transmit and then receives echoes from its own transmissions, or in dedicated transmit and receive modes in which ultrasound is transmitted by one of the diagnostic arrays and the resultant echoes received by the other diagnostic array for Doppler processing. Continuous wave techniques may thus be employed in this configuration.

Figure 7:
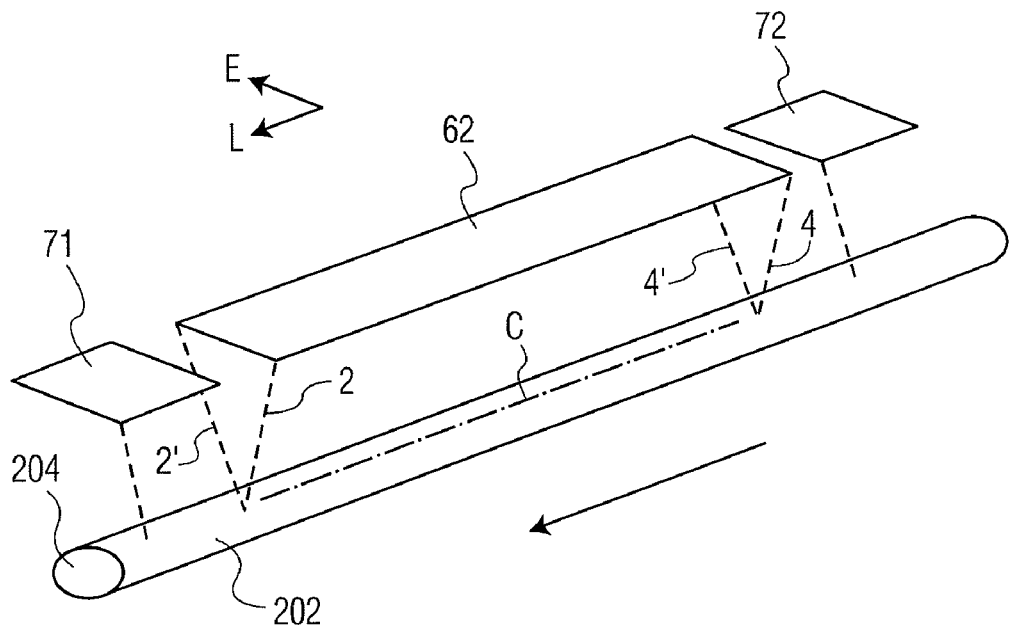
FIG. 7 illustrates a first method of using the transducer cuff of FIG. 3 to heat the blood of a located blood vessel.

FIG. 7 illustrates one technique for using the cuff 60 of FIG. 3 in accordance with the principles of the present invention. In the illustrated orientation the cuff position is adjusted until the "Flow" indicator indicates that a blood vessel is located beneath the diagnostic arrays 71,72. The therapy array 62 is then aligned with the axis of the blood vessel as indicated by the center line C. When the therapy array 62 is a two dimensional array segmented in the elevation dimension E, beams can be focused from along the therapy array 62 to the center C of the blood vessel 202. The exact center of the blood vessel along the length beneath the therapy array 62 can be determined by using a diagnostic array (not shown) on one or both sides of the therapy array, or by canting the diagnostic arrays 71,72 toward the area beneath the therapy array. For instance, each diagnostic array 71,72 could scan in from its end of the therapy array to the center of the array. The center C of the blood vessel 202 beneath the therapy array 62 can be found in this manner and heated along the entire length of the blood vessel beneath the array. This is a second approach to addressing heat dissipation by the flow of blood through the severed vessel 202.

Figure 8:
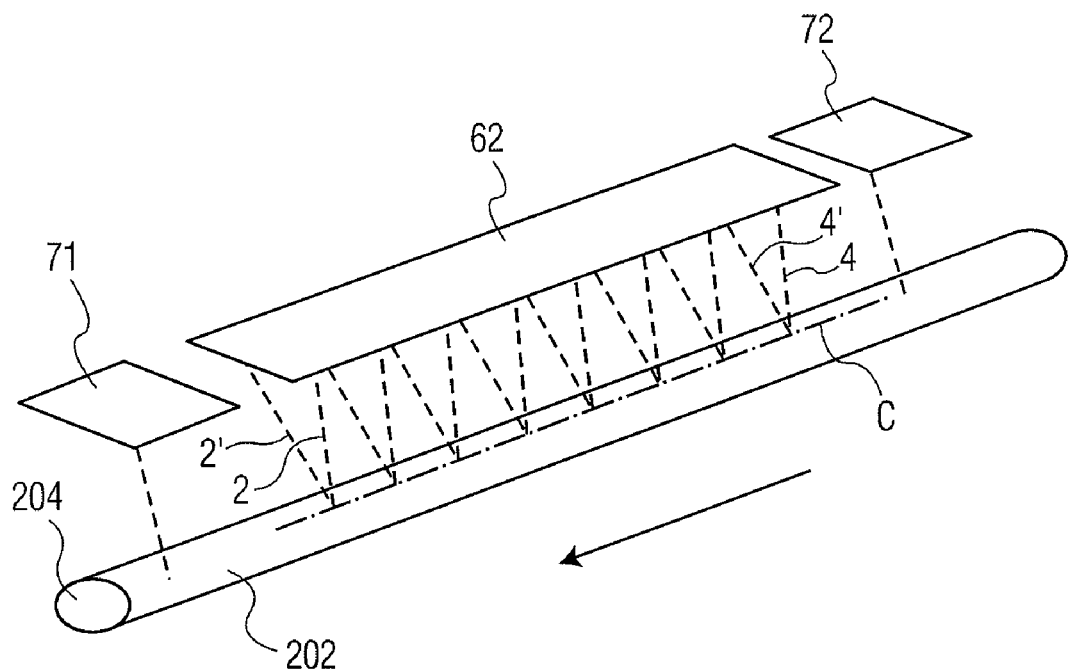
FIG. 8 illustrates a second method of using the transducer cuff of FIG. 3 to heat the blood of a located blood vessel.

FIG. 8 is similar to FIG. 7 except that in this example subgroups of elements of the therapy transducer 62 are focused in the azimuthal (longitudinal) direction rather than the elevational direction as done in FIG. 7. Different consecutive subgroups of therapy transducer elements along the array are focused at the center line C of the blood vessel 202, from the subgroup at one end of the array focusing beams between dashed lines 4-4' to the subgroup at the other end of the array focusing beams between dashed lines 2-2'.

Figure 9:
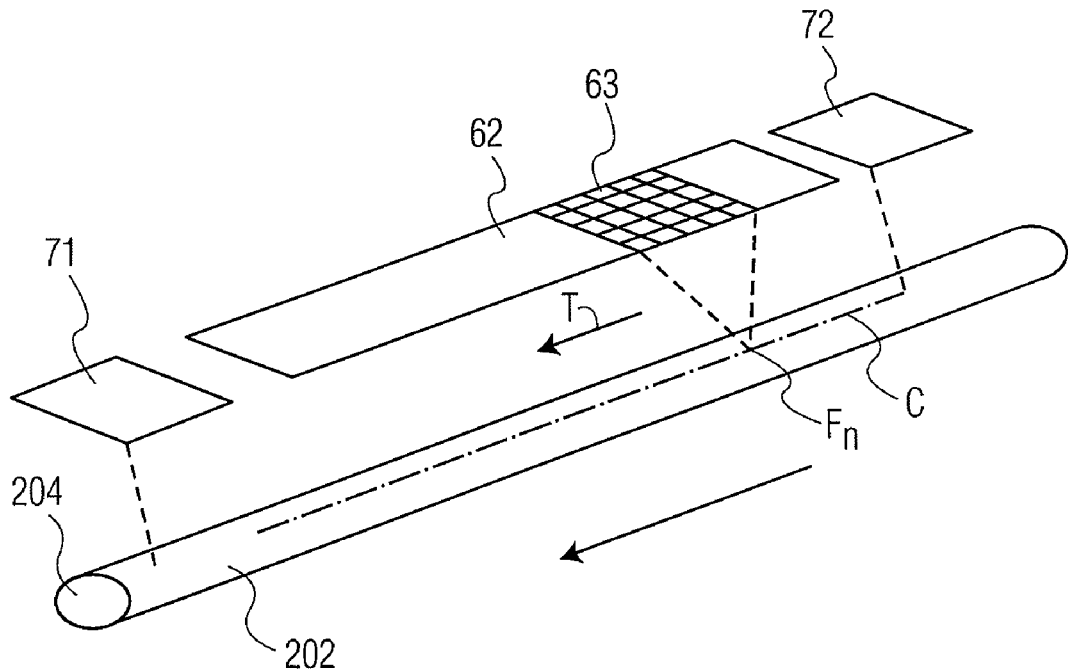
FIG. 9 illustrates a third method of using the transducer cuff of FIG. 3 to heat the blood of a located blood vessel.

FIG. 9 illustrates use of the transducer cuff of FIG. 3 to track and repeatedly heat a bolus of blood as it flows to the distal end 204 of the severed blood vessel 202. A bolus of blood is initially heated when it is located by the diagnostic array 72 at the proximal end of the therapy array 62. As the bolus flows to the distal end of the severed vessel 202 an activated subgroup 63 of therapy elements moves along the array 62 in the tracking direction T at the velocity of the flowing blood, thereby repeatedly heating the same bolus of blood as it traverses the blood vessel segment beneath the therapy array 62. The blood flow of the vessel is tracked through the length of the vessel by the diagnostic arrays 71,72 located at the longitudinal ends of the therapy array 62, and/or by diagnostic arrays located on one or both sides of the therapy array 62 (not shown).

Figure 10:
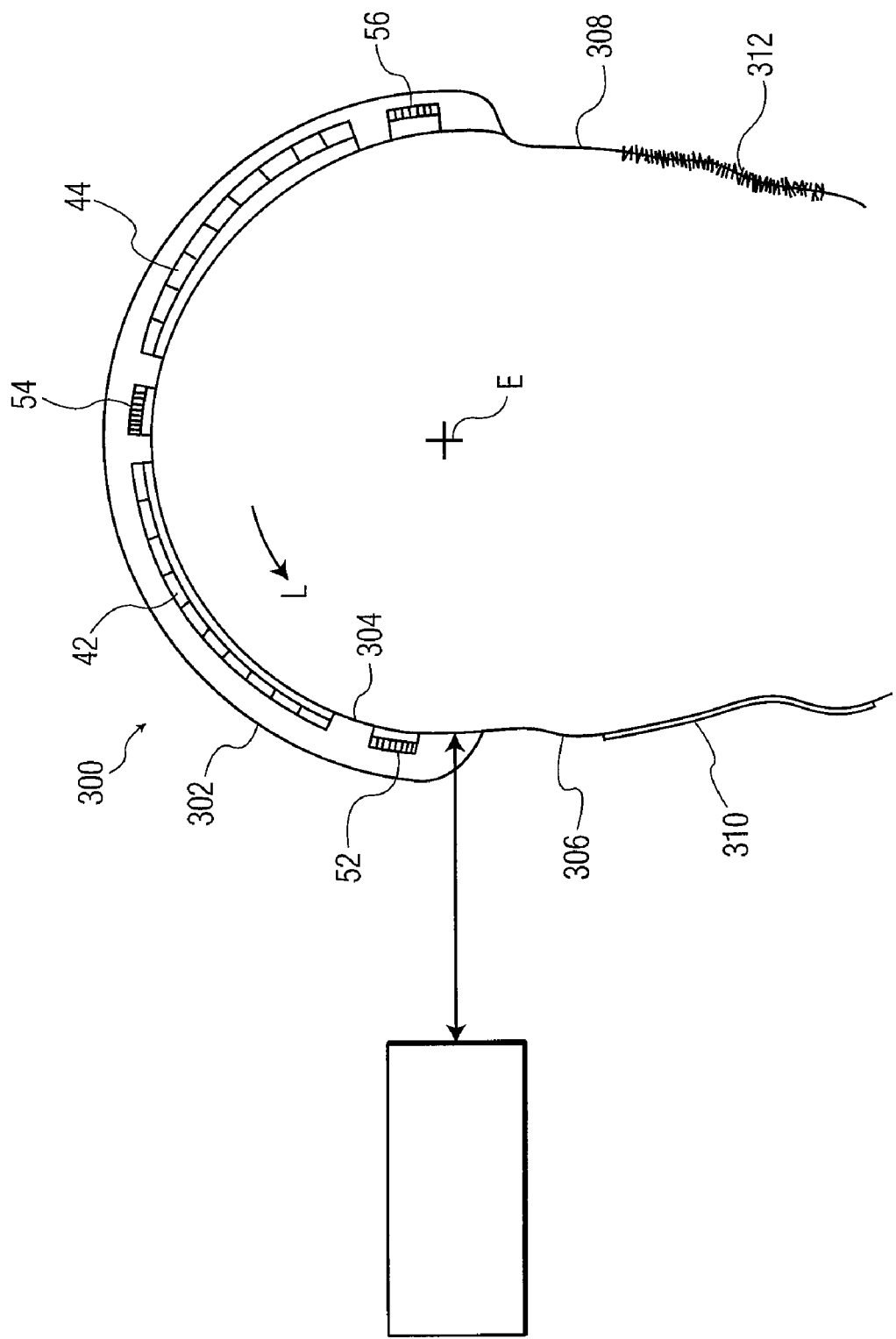
FIG. 10 illustrates a third example of a transducer cuff constructed in accordance with the principles of the present invention.

FIG. 10 illustrates a partial cuff 300 constructed in accordance with the principles of the present invention. The partial cuff 300, shown in cross-section in FIG. 10, has an inner surface 304 to which the transducer arrays 42-56 are connected and an outer surface 302 completing the enclosure of the transducer arrays. The space between the surfaces can be fluid-filled for acoustic coupling of the transducers, and/or acoustic coupling pads can be provided at the inner surface 304 as described previously. The partial array is attached to the limb of the patient by straps 306, 308 extending from the inner surface 304 at each end of the partial cuff. The straps can be secured together with a buckle or clip or other fastening means. In the example of FIG. 9 the straps. 306, 308 include complementary Velcro® surfaces 310 and 312, enabling the straps to be quickly and securely fastened tightly around the limb of a patient, then quickly opened and removed.

Figure 11:
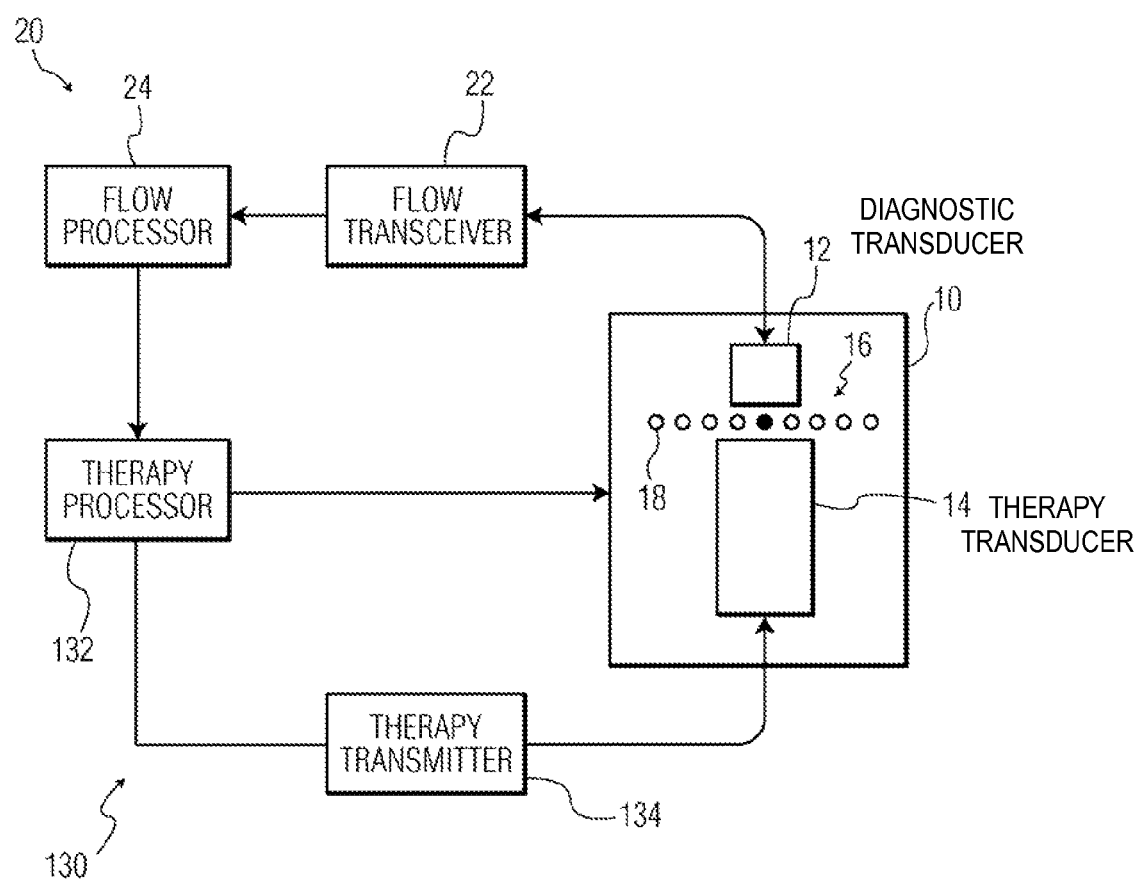
FIG. 11 illustrates an example of a system of the present invention which has a row of visual indicators to guide the user in placement of the transducer cuff in proximity to a blood vessel.

FIG. 11 illustrates an example of a diagnostic and therapy delivery system of the present invention with a display to help guide the user in successful location of the transducer cuff. In this example the cuff 10 includes at least one diagnostic array and at least one therapy array 14 as discussed in conjunction with FIG. 1. In this example the cuff is intended to be attached with the therapy array 14 parallel to and directly over a blood vessel of the injured limb. The parallel orientation is readily accomplished by virtue of the orientation of the therapy array 14 parallel to the axis of the transducer cuff. Alignment of the therapy array directly over a blood vessel is made possible by a line of indicators 16, in this example a row of LEDs. After the cuff is initially placed in acoustic contact with the limb, the diagnostic transducer 12 methodically scans the volume inside the cuff, searching for a strong and/or high velocity Doppler signal. When such blood flow is located, the lateral angle of the Doppler beam to the flow indicates the direction in which the cuff must be moved to locate the therapy array 14 directly over the blood vessel. For instance, if the blood vessel is to the left of the aligned diagnostic and therapy transducers, the Doppler beam will be angled to the left when directed at a sample volume in the vessel. Simple geometry then computes the distance which the cuff must be moved to bring the arrays directly over the blood vessel, at which point the Doppler beam will extend orthogonal to the emitting surface of the transducer when directed at the sample volume. An exact distance is not needed in this case, just the information that the cuff must be moved to the left, that is, the left/right direction of beam inclination. In the example of FIG. 11 the line 16 of LEDs extends laterally to the left and right of the therapy array 14. If the lateral distance of the leftward blood vessel is greater than the lateral distance from the center of the line of LEDs, indicated by the darkened LED, to the leftmost LED 18, the LED 18 is illuminated. The user now knows the cuff must be moved to the left. As the cuff is moved and the Doppler beam angle approaches orthogonality to the diagnostic array, the center of the therapy array will approach the location of the blood vessel and as it gets closer, more inward LEDs are lighted. Finally when the blood vessel is centered beneath the therapy array the center LED is illuminated. The change in the illuminated LED will thus quickly guide the user in correctly positioning the arrays over a blood vessel for most effective and efficient heating and coagulation.

It will be appreciated that the LED display 16 can be augmented with, or even replaced by, audible prompts from the system instructing the user to "move the cuff to the right" or "move the cuff to the left" and "stop" when the cuff is correctly positioned over a blood vessel.

Variations of the systems and techniques described above are within the scope of the present invention. For instance a heated bolus of blood may be tracked by receiving the strong harmonics emanating from the heated bolus with a diagnostic transducer, as described in U.S. Pat. No. 5,984,881 (Ishibashi et al.). Blood flow tracking may be performed by operating the therapy transducer in a receive mode. Other variations will readily occur to those skilled in the art.

What is claimed is:

1. An ultrasonic diagnostic and therapy system for reducing blood flow of a peripheral blood vessel by ultrasonic heating comprising:
   a transducer cuff configured for attachment to a limb, including at least one diagnostic transducer and at least one therapy transducer;
   a flow transceiver coupled to the diagnostic transducer for controlling a transmission of ultrasound by the diagnostic transducer and receiving echo signals from blood flow in response to the transmitted ultrasound;
   a flow processor coupled to the flow transceiver and responsive to the echo signals for identifying a location of blood flow;
   a therapy processor, responsive to the identification of a location of blood flow, for producing therapy control signals for the identified location; and
   a therapy transmitter, coupled to the therapy transducer, and operable to cause the therapy transducer to deliver high intensity focused ultrasound to the identified location of blood flow,
   wherein the therapy transmitter is operable to deliver high intensity focused ultrasound at intensity levels which produce heating at the identified location of blood flow, the therapy processor includes a therapy controller which acts to cause the therapy transducer to produce heat in a blood vessel until flow velocity in the vessel determined by the flow processor declines to an acceptable level, and the therapy controller acts to suspend the delivery of high intensity focused ultrasound by the therapy transducer while the diagnostic transducer acquires flow echo information.

2. The ultrasonic diagnostic and therapy system of claim 1, wherein the flow processor comprises a Doppler processor responsive to a receipt of Doppler echo signals for identifying a location of blood motion.

3. The ultrasonic diagnostic and therapy system of claim 2, wherein the Doppler processor produces estimates of flow velocity.

4. The ultrasonic diagnostic and therapy system of claim 1, wherein the flow transceiver controls the transmission of ultrasound by the diagnostic transducer to be within diagnostic imaging power limits.

5. The ultrasonic diagnostic and therapy system of claim 1, wherein the flow processor operates to identify a location of blood flow in three dimensional space.

6. The ultrasonic diagnostic and therapy system of claim 1, wherein the therapy processor is responsive to signals from the flow processor which indicate vessel size, flow velocity in the vessel, and flow location in the vessel.

7. The ultrasonic diagnostic and therapy system of claim 1, wherein the therapy processor produces control signals which control the power delivered by the therapy transducer, the time of actuation of the therapy transducer, and the focal point of delivered high intensity focused ultrasound.

8. The ultrasonic diagnostic and therapy system of claim 1, wherein the transducer cuff exhibits a controllable pressure which acts to control the contact of the transducers with the limb.

9. The ultrasonic diagnostic and therapy system of claim 8, wherein the transducer cuff exhibits a controllable high pressure which acts to restrict blood flow through blood vessels of the limb.

10. The ultrasonic diagnostic and therapy system of claim 8, wherein the transducer cuff exhibits a controllable high pressure which acts to increase the acoustic coupling between the transducers and the limb.

11. The ultrasonic diagnostic and therapy system of claim 8, wherein the transducer cuff exhibits a controllable high pressure which acts to stabilize the position of the transducers with respect to blood vessels in the limb.

12. The ultrasonic diagnostic and therapy system of claim 1, further comprising a display responsive to the flow processor which is actuated to indicate that a location of blood flow has been identified.

13. The ultrasonic diagnostic and therapy system of claim 12, wherein the display comprises one or more light emitting devices.

14. The ultrasonic diagnostic and therapy system of claim 13, wherein the display comprises a two or three dimensional image display.

15. The ultrasonic diagnostic and therapy system of claim 1, further comprising an audible emitter responsive to the flow processor which is actuated to indicate that a location of blood flow has been identified.

16. The ultrasonic diagnostic and therapy system of claim 15, wherein the audible emitter is further responsive to the flow processor for guiding the placement of the transducer cuff.

* * * * *